US011042174B2

(12) United States Patent
Sahu et al.

(10) Patent No.: US 11,042,174 B2
(45) Date of Patent: Jun. 22, 2021

(54) SYSTEM AND METHOD FOR THERMAL MANAGEMENT OF A WEARABLE COMPUTING DEVICE BASED ON PROXIMITY TO A USER

(71) Applicant: QUALCOMM INCORPORATED, San Diego, CA (US)

(72) Inventors: Vivek Sahu, San Diego, CA (US); Don Le, San Diego, CA (US); Jon Anderson, Boulder, CO (US); Peng Wang, San Diego, CA (US); Shujuan Wang, San Diego, CA (US)

(73) Assignee: Qualcomm Incorporated, San Diego, CA (US)

( * ) Notice: Subject to any disclaimer, the term of this patent is extended or adjusted under 35 U.S.C. 154(b) by 0 days.

(21) Appl. No.: 15/424,661

(22) Filed: Feb. 3, 2017

(65) Prior Publication Data

US 2018/0224871 A1   Aug. 9, 2018

(51) Int. Cl.
*G05D 23/19* (2006.01)
*A61B 5/1455* (2006.01)
*A61B 5/00* (2006.01)
*G06F 1/3231* (2019.01)
*G06F 1/20* (2006.01)
(Continued)

(52) U.S. Cl.
CPC ..... *G05D 23/1927* (2013.01); *A61B 5/14552* (2013.01); *A61B 5/6844* (2013.01); *G05D 23/1917* (2013.01); *G06F 1/163* (2013.01); *G06F 1/206* (2013.01); *G06F 1/3231* (2013.01); *H04W 52/0254* (2013.01);
(Continued)

(58) Field of Classification Search
None
See application file for complete search history.

(56) References Cited

U.S. PATENT DOCUMENTS 8,180,583 B1    5/2012  Gossweiler et al.
2013/0090888 A1 4/2013  Anderson et al.
(Continued)

OTHER PUBLICATIONS

Watthanawisuth et al., "Wireless Wearable Pulse Oximeter for Health Monotoring using ZigBee Wireless Sensor Network", IEEE 2010 (Year: 2010).*
(Continued)

*Primary Examiner* — Carlos R Ortiz Rodriguez
(74) *Attorney, Agent, or Firm* — Edward Meisarosh

(57) ABSTRACT

Because the touch temperature of a wearable computing device ("WCD") may be an insignificant factor for user experience when the WCD is not being worn by a user, embodiments of the solution seek to modify thermal management policies based on an inferred user proximity state. Exemplary embodiments monitor one or more signals from readily available sensors in the WCD that have primary purposes other than measuring user proximity. Depending on embodiment, the sensors may be selected from a group consisting of a heart rate monitor, a pulse monitor, an O2 sensor, a bio-impedance sensor, a gyroscope, an accelerometer, a temperature sensor, a pressure sensor, a capacitive sensor, a resistive sensor and a light sensor. Using the signals generated by such sensors, relative physical proximity of the WCD to a user may be inferred and, based on the user proximity state, thermal policies either relaxed or tightened.

40 Claims, 9 Drawing Sheets

(51) Int. Cl.
  *H04W 52/02* (2009.01)
  *G06F 1/16* (2006.01)
(52) U.S. Cl.
  CPC ......... *H04W 52/0261* (2013.01); *Y02D 10/00* (2018.01); *Y02D 30/70* (2020.08)

(56) References Cited

U.S. PATENT DOCUMENTS

| | | |
|---|---|---|
| 2014/0262161 A1 | 9/2014 | Weigand |
| 2014/0266780 A1 | 9/2014 | Rahman et al. |
| 2015/0187206 A1 | 7/2015 | Saurin et al. |
| 2015/0192976 A1 | 7/2015 | Jeganathan et al. |
| 2016/0091938 A1* | 3/2016 | Edwards ................. G06F 1/206 700/300 |
| 2016/0157718 A1 | 6/2016 | Barnes et al. |
| 2016/0174913 A1 | 6/2016 | Somanath et al. |

OTHER PUBLICATIONS

International Search Report and Written Opinion—PCT/US2018/016501—ISA/EPO—dated May 2, 2018.

* cited by examiner

NEAR TO USER STATE — 405

- TEMPERATURE THRESHOLD DICTATED BY TOUCH TEMPERATURE LIMIT OF DEVICE
- THERMAL MANAGEMENT POLICIES MAY INCLUDE THERMAL MITIGATION TECHNIQUES FOR SACRIFICING PERFORMANCE IN FAVOR OF LOWER OPERATING TEMPERATURE
- MAXIMUM QoS AS DEFINED BY PERFORMANCE SUBJECT TO TOUCH TEMPERATURE

AWAY FROM USER STATE — 410

- TEMPERATURE THRESHOLD DICTATED BY OPERATING TEMPERATURE OF COMPONENTS SUBJECT TO A MODESTLY INCREASED TOUCH TEMPERATURE LIMIT
- THERMAL MANAGEMENT POLICIES MAY INCLUDE THERMAL MITIGATION TECHNIQUES FOR INCREASING PERFORMANCE OF THE DEVICE AT THE EXPENSE OF INCREASED THERMAL ENERGY GENERATION
- IMPROVED QoS AS DEFINED BY PERFORMANCE

DOCKED STATE — 415

- TEMPERATURE THRESHOLD DICTATED BY OPERATING TEMPERATURE LIMITS OF COMPONENTS
- THERMAL MANAGEMENT POLICIES MAY INCLUDE TECHNIQUES FOR MAXIMIZING PERFORMANCE OF THE DEVICE AT THE EXPENSE OF SUBSTANTIAL THERMAL ENERGY GENERATION
- MAXIMUM QoS AS DEFINED BY PERFORMANCE

*FIG. 5*

SYSTEM AND METHOD FOR THERMAL MANAGEMENT OF A WEARABLE COMPUTING DEVICE BASED ON PROXIMITY TO A USER

DESCRIPTION OF THE RELATED ART

Wearable computing devices ("WCDs") are becoming ubiquitous in today's society. These devices, which may also be called "wearable gadgets" or simply "wearables," may be worn for any number of primary reasons, but commonly they are worn for health monitoring and fitness tracking.

One unique aspect of WCDs is that they do not have active cooling devices, like fans, as are often found in larger computing devices such as laptop and desktop computers. Instead of using fans, WCDs may rely on strategic placement of passive cooling devices and/or spatial arrangement of electronic packaging so that two or more active and heat producing components are not positioned proximally to one another. When two or more heat producing components are suitably spaced from one another within a WCD, thermal energy generated from the operation of each component may not combine to cause temperatures that can negatively impact user experience.

The reality, however, is that WCDs are inevitably very limited in size and, therefore, room for components within a WCD often comes at a premium. As such, there just typically is not enough space within a WCD for engineers and designers to control temperature through spatial arrangements or placement of passive cooling components. Therefore, to reduce thermal energy generation within a WCD, engineers and designers often leverage one or more thermal mitigation techniques that essentially trade off WCD performance for a lower rate of thermal energy generation. Implementation of a thermal mitigation technique is usually triggered by temperature measurements within the WCD.

In most WCDs today, the trigger temperature for applying a thermal mitigation technique is linked to the "touch temperature" of the device and not the temperature of any given component within the WCD. That is, most WCDs today are capable of efficiently running at a temperature level that exceeds the temperature considered to be acceptable for contact with a user. Notably, therefore, WCD performance is often sacrificed unnecessarily by applying thermal mitigation techniques when the WCD is not proximal to a user.

Accordingly, what is needed in the art is a method and system for leveraging the proximity of a WCD to its user so that thermal energy generated by the WCD may be managed intelligently without over-impacting its performance and functionality. More specifically, what is needed in the art is a method and system that leverages one or more sensors in a WCD from which, among other things, physical contact (or lack of physical contact) with a user may be inferred and, in view of the inference, intelligently manages thermal energy generation within the WCD.

SUMMARY OF THE DISCLOSURE

Various embodiments of methods and systems for leveraging a user proximity measurement to determine thermal management policies implemented in a wearable computing device ("WCD") are disclosed. Notably, in many WCDs, the "touch temperature" of the external surfaces of the device limits the extent to which the performance capabilities of the WCD can be exploited. Generally, as more power is consumed by the various components of a WCD, the resulting generation of thermal energy can cause the external temperatures of the WCD to detrimentally affect user experience.

Because the touch temperature of a WCD may be an insignificant factor for user experience when the WCD is not physically proximal to a user, one such method for determining thermal management policies based on a user proximity measurement involves monitoring one or more signals from readily available sensors in the WCD that have primary purposes other than measuring user proximity. Depending on embodiment, the sensors may be selected from a group consisting of a heart rate monitor, a pulse monitor, an O2 sensor, a bio-impedance sensor, a gyroscope, an accelerometer, a temperature sensor, a pressure sensor, a capacitive sensor, a resistive sensor and a light sensor. Using the signals generated by such sensors, the method may infer relative physical proximity of the WCD to a user.

With the sensor readings and sensor types recognized, the method may categorize the one or more signals into predefined and ranked categories and, based on the monitored one or more signals in a highest ranked category, determine a user proximity state for the WCD. Subsequently, based on the user proximity state the method may set a first temperature threshold for triggering initiation of one or more thermal management policies, wherein the first temperature threshold is associated with a first temperature sensor in the WCD. Then, the method may compare the first temperature threshold with a temperature measurement received from the first temperature sensor. Based on the comparison, the method may evaluate the applicability of currently implemented thermal management policies and elect to either maintain those policies or modify them in view of the user proximity state.

For instance, if the temperature threshold is higher than the actual measurement, thermal management policies that allow one or more components to increase power consumption, even though more thermal energy will be generated and dissipated as a result, can be implemented and quality of service ("QoS") increased. Similarly, if the temperature threshold is lower or near the actual temperature measurement, thermal mitigation techniques may be implemented to reduce the thermal energy generation, thereby causing QoS to suffer but improving user experience by lowering the temperature of the WCD.

Advantageously, as one of ordinary skill in the art will recognize, by leveraging a user proximity state determination to set temperature thresholds of the WCD, the QoS provided by the WCD can be optimized when touch temperature of the WCD is not a significant factor for user experience.

BRIEF DESCRIPTION OF THE DRAWINGS

In the drawings, like reference numerals refer to like parts throughout the various views unless otherwise indicated. For reference numerals with letter character designations such as "102A" or "102B", the letter character designations may differentiate two like parts or elements present in the same figure. Letter character designations for reference numerals may be omitted when it is intended that a reference numeral to encompass all parts having the same reference numeral in all figures.

FIG. 5 is a diagram illustrating exemplary thermal management policies and associated conditions that may be leveraged by the thermal policy manager module in FIG. 1 and are dependent upon a particular user proximity state illustrated in FIG. 4;

DETAILED DESCRIPTION

Figure 1:
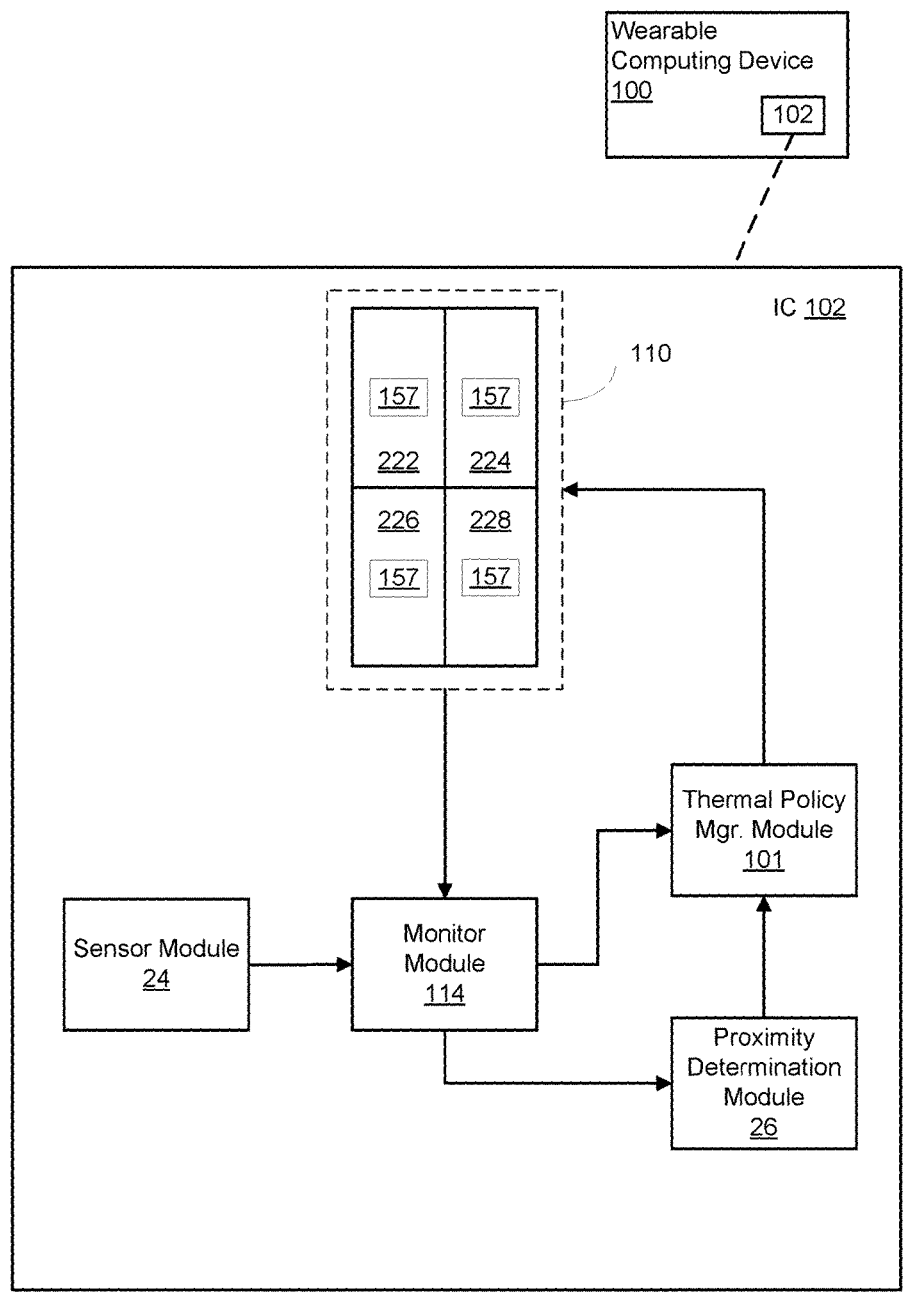
FIG. 1 is a functional block diagram illustrating an embodiment of an on-chip system for implementing proximity based thermal management in a wearable computing device ("WCD")

The word "exemplary" is used herein to mean "serving as an example, instance, or illustration." Any aspect described herein as "exemplary" is not necessarily to be construed as exclusive, preferred or advantageous over other aspects.

In this description, the term "application" may also include files having executable content, such as: object code, scripts, byte code, markup language files, and patches. In addition, an "application" referred to herein, may also include files that are not executable in nature, such as documents that may need to be opened or other data files that need to be accessed.

As used in this description, the terms "component," "database," "module," "system," "thermal energy generating component," "processing component" and the like are intended to refer to a computer-related entity, either hardware, firmware, a combination of hardware and software, software, or software in execution. For example, a component may be, but is not limited to being, a process running on a processor, a processor, an object, an executable, a thread of execution, a program, and/or a computer. By way of illustration, both an application running on a computing device and the computing device may be a component. One or more components may reside within a process and/or thread of execution, and a component may be localized on one computer and/or distributed between two or more computers. In addition, these components may execute from various computer readable media having various data structures stored thereon. The components may communicate by way of local and/or remote processes such as in accordance with a signal having one or more data packets (e.g., data from one component interacting with another component in a local system, distributed system, and/or across a network such as the Internet with other systems by way of the signal).

In this description, the terms "central processing unit ("CPU")," "digital signal processor ("DSP")," "graphical processing unit ("GPU")," and "chip" are used interchangeably. Moreover, a CPU, DSP, GPU or a chip may be comprised of one or more distinct processing components generally referred to herein as "core(s)." Additionally, to the extent that a CPU, DSP, GPU, chip or core is a functional component within a WCD that consumes various levels of power to operate at various levels of functional efficiency, one of ordinary skill in the art will recognize that the use of these terms does not limit the application of the disclosed embodiments, or their equivalents, to the context of processing components within a WCD. That is, although many of the embodiments are described in the context of a processing component, it is envisioned that thermal policies triggered by proximity determinations derived from various sensor measurements may be applied to any functional component that may be within a given WCD including, but not limited to, a modem, a camera, a wireless network interface controller ("WNIC"), a display, a video encoder, a peripheral device, etc.

In this description, it will be understood that the terms "thermal" and "thermal energy" may be used in association with a device or component capable of generating or dissipating energy that can be measured in units of "temperature." Consequently, it will further be understood that the term "temperature," with reference to some standard value, envisions any measurement that may be indicative of the relative warmth, or absence of heat, of a "thermal energy" generating device or component. For example, the "temperature" of two components is the same when the two components are in "thermal" equilibrium.

In this description, the terms "workload," "process load" and "process workload" are used interchangeably and generally directed toward the processing burden, or percentage of processing burden, associated with a given processing component in a given embodiment. Further to that which is defined above, a "processing component" or "thermal energy generating component" or "thermal aggressor" may be, but is not limited to, a central processing unit, a graphical processing unit, a core, a main core, a sub-core, a processing area, a hardware engine, etc. or any component residing within, or external to, an integrated circuit within a wearable computing device. Moreover, to the extent that the terms "thermal load," "thermal distribution," "thermal signature," "thermal processing load" and the like are indicative of workload burdens that may be running on a thermal aggressor, one of ordinary skill in the art will acknowledge that use of these "thermal" terms in the present disclosure may be related to process load distributions, workload burdens and power consumption.

In this description, the terms "thermal mitigation technique(s)," "thermal policies," "thermal management," "thermal mitigation measure(s)" and "throttling strategy" are used interchangeably. Notably, one of ordinary skill in the art will recognize that, depending on the particular context of use, any of the terms listed in this paragraph may serve to describe hardware and/or software operable to increase performance at the expense of thermal energy generation, decrease thermal energy generation at the expense of performance, or alternate between such goals.

In this description, the term "wearable computing device" ("WCD") is used to describe any device operating on a limited capacity power supply, such as a battery. Although WCDs are most generally recognized as wrist-worn health and fitness tracking devices that may be either a "standalone" device or a device that wirelessly syncs with a mobile phone or remote server in order to fully render its intended functionality, a WCD is not limited to such wearable fitness devices. Indeed, a WCD may be any device capable of being worn on a user's person and comprising sensors from which a user's physical proximity may be inferred. Therefore, a WCD may be a cellular telephone, a pager, a PDA, a smartphone, a navigation device, a wrist watch, a fitness tracker, a media player, a tech gadget (e.g., a smartwatch, a health monitor, smart glasses, activity tracker, etc.), a combination of the aforementioned devices, among others.

Managing thermal energy generation in a WCD, without unnecessarily impacting quality of service ("QoS"), can be accomplished by leveraging one or more sensor measurements within the WCD that can be used to indicate, deduce or infer proximity of the WCD to its user—I.e., whether the WCD is being worn by its user. Advantageously, WCDs already include sensor modules containing various combinations of sensors and associated hardware and/or software for monitoring, recording and rendering data related to, among other things, one or more of heart rate, pulse, blood oxygen saturation, bio-impedance, global positioning coordinates, rotational motion (gyroscope), acceleration force (accelerometer), temperature, pressure, capacitance, resistance, motion, specific absorption rate, light, etc. This sensor module hardware and/or software is leveraged in some embodiments of the present solution to detect if the WCD has been positioned within close proximity of a user, such as on the user's wrist or arm, as a trigger for determining and applying thermal management policies within the WCD.

In embodiments of the system and method for proximity based thermal management, sensor modules in the WCD for some primary purpose other than determining user proximity may be used by the WCD for the secondary purpose of triggering throttling strategies that optimize WCD performance subject to acceptable temperature ranges for user contact (or lack of user contact). Basically, if the WCD is not being worn by its user, embodiments of the solution provide for relaxation of thermal algorithms that results in an increased performance. Conversely, if the WCD is being worn, embodiments of the solution provide for selection and execution of more relatively conservative thermal policies. Moreover, when the WCD is not being worn by its user, it is envisioned that embodiments of the solution may provide for certain tasks to be performed automatically, such as downloading or uploading files to the "cloud" or a complimentary portable computing device or a remote server, syncing the WCD, updating software, or any task not necessarily requiring user intervention.

As generally described above, throttling strategies are various methods, applications and/or algorithms that may be employed by the WCD to increase its performance through adjustment of hardware and/or software parameters, such as the clock speed of a central processing unit ("CPU") or the like. Certain throttling strategies may increase performance of a WCD at the expense of increased thermal energy generation; however, certain other throttling strategies may mitigate a detrimental rise in operating temperature by reducing or prioritizing WCD performance.

In various embodiments, the sensor module may be used by the WCD to dictate the application of certain throttling strategies that increase the performance efficiency of the WCD when it is not in direct contact or in close proximity to a user. Conversely, embodiments may also leverage the sensor module to trigger the implementation of throttling strategies that operate to prevent the WCD from generating heat above temperature thresholds that are acceptable for human contact.

Further, it is envisioned that certain embodiments of the solution may include false detection logic implemented in software and/or hardware. For those embodiments that include false detection logic, a sensor reading or combination of sensor readings from which it may be inferred that the WCD is being worn by a user could be "overruled" by a complimentary sensor reading that indicates otherwise. For example, GPS readings indicating that the WCD is changing location (and, thus, being worn by a user) may be overruled by an accelerometer reading indicating that the WCD is stationary (such as may be the case if the WCD is not being worn by a user while in a moving object like a car).

Notably, although embodiments of the solution are described herein within the context of a WCD either being "worn" or "not worn," i.e. described within the context of a binary use case, the scope of the solution is not limited to binary applications. That is, it is envisioned that exemplary embodiments of the solution may leverage a multiple stage detection logic that can, in turn, be used to further optimize thermal policy selection and implementation. For example, certain embodiments may further characterize the device state, beyond simply whether it is being worn or not, to include other states such as, but not limited to, the WCD has just been adorned by the user, the WCD has been worn for an extended period of time, the WCD has just been removed from the user's person, the WCD has been removed from the user's person for an extended period of time, etc. Based on a recognition or inference of a given stage or state from a logical reconciliation of multiple sensor readings, an embodiment of the solution may further optimize a mitigation policy over an embodiment that simply infers "worn" or "not worn" states. For example, if a WCD that leverages multiple stage detection infers that it has been worn by a user for a relatively long duration, a thermal policy temperature threshold otherwise suitable for a short duration of user contact may be lowered accordingly. Or, as another example, if a WCD that leverages multiple stage detection infers that it has just been removed from direct contact with a user, it may implement a waiting period before increasing performance thresholds or beginning execution of a certain automated task.

FIG. 1 is a functional block diagram illustrating an exemplary embodiment of an on-chip system 102 for proximity based thermal management in a wearable computing device 100. To set temperature thresholds for triggering the application of one or more thermal mitigation techniques, the on-chip system 102 may leverage temperature sensors 157 and various sensors in sensor module 24 for detecting proximity of the WCD 100 to a user and measuring temperatures associated with processing components 110. Advantageously, by defining and updating acceptable temperature thresholds based on proximity of the WCD 100 to a user, the QoS experienced by a user of the WCD may be optimized when not worn by avoiding unnecessary throttling of the CPU 110 triggered by preset, over-restrictive temperature thresholds.

In general, the system employs two main modules which, in some embodiments, may be contained in a single module: (1) a proximity determination ("PD") module 26 for determining the WCD's state of proximity to a user and adjusting temperature thresholds in view of the determined state of proximity; and (2) a thermal policy manager ("TPM") module 101 for implementing throttling strategies based on the temperature threshold set by the PD module 26. Advantageously, embodiments of the system and method that include the two main modules leverage sensor data from which user proximity may be inferred to capitalize on opportunities for processing components 110 within the WCD 100 to consume more power, and thus generate more thermal energy, when the touch temperature, i.e. the outer temperature of the WCD 100 exposed to a user, is not a significant or relevant factor of user experience.

To recognize a state of user proximity, the PD module 26 may receive a signal from a monitor module 114 that is in communication with one or more sensors associated with a sensor module 24. Sensors in sensor module 24 may include, but are not limited to including, sensors configured for the measurement of heart rate, pulse rate, blood oxygen saturation, bio-impedance, global positioning coordinates, rotational motion (gyroscope), acceleration force (accelerometer), temperature, pressure, capacitance, resistance, motion, specific absorption rate, and light.

Some embodiments of a sensor in a sensor module 24 may be configured to emit an electromagnetic field and recognize a disturbance in the field that indicates user proximity to the WCD 100. Similarly, other sensors in a sensor module 24 may generate an electromagnetic transmission (e.g., infra-red) and recognize a return transmission that reflects from a proximal user. Still other embodiments may leverage gyroscopes or accelerometers in a sensor module 24 to deduce a user's presence based on movement of the WCD 100. Still other embodiments may leverage pulse oximeters in a sensor module 24 to deduce a user's presence based on recognition of a blood oxygen saturation level and/or other plethysmographic data such as a pulse.

Returning to the FIG. 1 illustration, having received signals from the monitor module 114 from one or more sensors of the sensor module 24, the PD module 26 may prioritize the readings from the various sensors based on a predefined ranking system. In view of the rankings, the PD module 26 may then apply rules in order to determine whether the WCD 100 is, or is not, being worn by a user (I.e., determine the "user proximity state" of the WCD). For example, an exemplary rule may dictate that the PD module 26 determine the user proximity state solely on a value of a reading generated by a pulse oximeter if a pulse oximeter is associated with the sensor module 24 and identified as "online" by the monitor module 114. As another example, an exemplary rule may dictate that the PD module 26 determine the user proximity state based on an "if/then" logic that considers combinations of readings from multiple sensors associated with the sensor module 24.

Using predefined rules that give weighted value to readings from sensors associated with sensor module 24 depending upon the type of sensor and its output, the PD module 26 may conclude under certain scenarios that the WCD 100 is not proximal to a user. Notably, when the WCD 100 is not physically in contact with a user, the touch temperature of the WCD 100 is not a significant factor of user experience in the short term. As such, even though increased thermal energy dissipation may cause the touch temperature of the WCD 100 to exceed a default threshold deemed acceptable for user exposure while the WCD 100 is being worn, the various processing cores 222, 224, 226, 228 of the multi-core processing component 110 may increase processing capacity to provide a higher QoS because the touch temperature threshold is not a primary determinant for acceptable levels of thermal energy generation in the immediate short term.

Returning to the exemplary scenario of a user proximity state that indicates the user is physically away from the WCD 100, the PD module 26 may communicate with the TPM module 101 to override or adjust a default temperature threshold associated with acceptable touch temperature of the WCD 100. In adjusting the temperature threshold, the PD module 26 may set a new, higher temperature threshold associated with temperature limits of one or more components of the WCD 100. Subsequently, the TPM module 101 may receive temperature readings from the monitor module 114 indicating temperature levels sensed by sensors 157 which may be associated with a skin temperature of the WCD 100 and/or individually or collectively with one or more various processing components 222, 224, 226, 228. Based on the temperature readings from sensors 157 and the new, higher temperature threshold set by the PD module 26, the TPM 101 may implement thermal management techniques to optimize processing performance in view of thermal energy dissipation.

Figure 2:
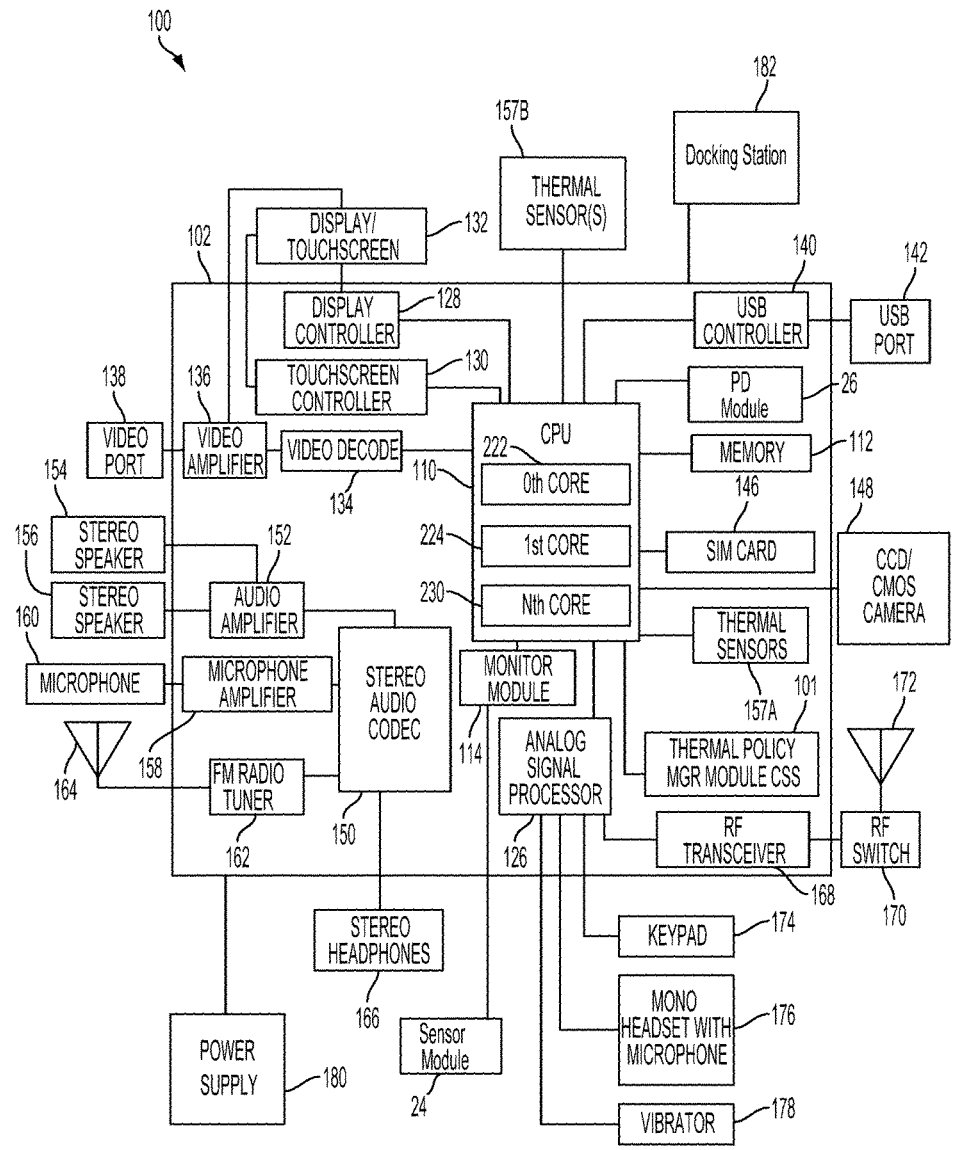
FIG. 2 is a functional block diagram illustrating an exemplary, non-limiting aspect of the WCD of FIG. 1 in the form of a wireless telephone for implementing methods and systems for monitoring thermal conditions, adjusting temperature thresholds based on user proximity and triggering application of thermal mitigation measures based on the adjusted thresholds.

FIG. 2 is a functional block diagram illustrating an exemplary, non-limiting aspect of the WCD 100 of FIG. 1 in the form of a wireless telephone for implementing methods and systems for monitoring thermal conditions, adjusting temperature thresholds based on user proximity and triggering application of thermal mitigation measures based on the adjusted thresholds. Notably, the aspect of a WCD 100 depicted in FIG. 2 is for exemplary purposes only and is not meant to suggest that all WCDs are in the form of a wireless telephone or comprise all of the various components depicted in the exemplary FIG. 2 aspect. Indeed, it is envisioned that most WCDs that form a part of an embodiment of the solution will comprise some subset of the components and associated functionality suggested by the FIG. 2 aspect. As described above, a WCD 100 may, in fact, be in the form of a wireless telephone but also may take other forms such as, but not limited to, a wearable tech gadget in the form of a smartwatch, or a health monitor, or smart glasses, or activity tracker, or fitness device, etc.

As shown, the WCD 100 includes an on-chip system 102 that includes a multi-core central processing unit ("CPU") 110 and an analog signal processor 126 that are coupled together. The CPU 110 may comprise a zeroth core 222, a first core 224, and an Nth core 230 as understood by one of ordinary skill in the art. Further, instead of a CPU 110, a digital signal processor ("DSP") may also be employed as understood by one of ordinary skill in the art.

In general, the TPM module(s) 101 may be responsible for monitoring and applying thermal policies that may help a WCD 100 manage thermal conditions and/or thermal loads and avoid experiencing adverse thermal conditions, such as, for example, reaching critical temperatures, while maintaining a high level of functionality.

FIG. 2 also shows that the WCD 100 may include a monitor module 114. The monitor module 114 communicates with multiple operational sensors (e.g., thermal sensors 157) distributed throughout the on-chip system 102 and with the CPU 110 of the WCD 100 as well as with the TPM module 101. The monitor module 114 may also monitor signals generated by sensors in sensor module 24 and transmit the signal, or data representative of the signal, to the PD module 26. The sensor readings from sensor module 24 may be used to determine or infer user proximity to the WCD 100. The TPM module 101 may work with the monitor module 114 to identify adverse thermal conditions relative to temperature thresholds set by PD module 26 and apply one or more thermal mitigation techniques to manage thermal aggressors within chip 102.

As illustrated in FIG. 2, a display controller 128 and a touch screen controller 130 are coupled to the digital signal processor 110. A touch screen display 132 external to the on-chip system 102 is coupled to the display controller 128 and the touch screen controller 130.

WCD 100 may further include a video encoder 134, e.g., a phase-alternating line ("PAL") encoder, a sequential couleur avec memoire ("SECAM") encoder, a national television system(s) committee ("NTSC") encoder or any other type of video encoder 134. The video encoder 134 is coupled to the multi-core central processing unit ("CPU") 110. A video amplifier 136 is coupled to the video encoder 134 and the touch screen display 132. A video port 138 is coupled to the video amplifier 136. As depicted in FIG. 2, a universal serial bus ("USB") controller 140 is coupled to the CPU 110. Also, a USB port 142 is coupled to the USB controller 140. A memory 112 and a subscriber identity module ("SIM") card 146 may also be coupled to the CPU 110. Further, as shown in FIG. 2, a digital camera 148 may be coupled to the CPU 110. In an exemplary aspect, the digital camera 148 is a charge-coupled device ("CCD") camera or a complementary metal-oxide semiconductor ("CMOS") camera.

As further illustrated in FIG. 2, a stereo audio CODEC 150 may be coupled to the analog signal processor 126. Moreover, an audio amplifier 152 may be coupled to the stereo audio CODEC 150. In an exemplary aspect, a first stereo speaker 154 and a second stereo speaker 156 are coupled to the audio amplifier 152. FIG. 2 shows that a microphone amplifier 158 may be also coupled to the stereo audio CODEC 150. Additionally, a microphone 160 may be coupled to the microphone amplifier 158. In a particular aspect, a frequency modulation ("FM") radio tuner 162 may be coupled to the stereo audio CODEC 150. Also, an FM antenna 164 is coupled to the FM radio tuner 162. Further, stereo headphones 166 may be coupled to the stereo audio CODEC 150.

FIG. 2 further indicates that a radio frequency ("RF") transceiver 168 may be coupled to the analog signal processor 126. An RF switch 170 may be coupled to the RF transceiver 168 and an RF antenna 172. As shown in FIG. 2, a keypad 174 may be coupled to the analog signal processor 126. Also, a mono headset with a microphone 176 may be coupled to the analog signal processor 126. Further, a vibrator device 178 may be coupled to the analog signal processor 126. FIG. 2 also shows that a power supply 180, for example a battery, is coupled to the on-chip system 102. In a particular aspect, the power supply includes a rechargeable DC battery or a DC power supply that is derived from an alternating current ("AC") to DC transformer that is connected to an AC power source.

The CPU 110 may also be coupled to one or more internal, on-chip thermal sensors 157A as well as one or more external, off-chip thermal sensors 157B. The on-chip thermal sensors 157A may comprise one or more proportional to absolute temperature ("PTAT") temperature sensors that are based on vertical PNP structure and are usually dedicated to complementary metal oxide semiconductor ("CMOS") very large-scale integration ("VLSI") circuits. The off-chip thermal sensors 157B may comprise one or more thermistors. The thermal sensors 157 may produce a voltage drop that is converted to digital signals with an analog-to-digital converter ("ADC") controller 103 (See FIG. 3A). However, other types of thermal sensors 157 may be employed without departing from the scope of the invention.

The thermal sensors 157, in addition to being controlled and monitored by an ADC controller 103, may also be controlled and monitored by one or more TPM module(s) 101. The TPM module(s) may comprise software that is executed by the CPU 110. However, the TPM module(s) 101 may also be formed from hardware and/or firmware without departing from the scope of the invention. The TPM module(s) 101 may be responsible for monitoring and applying thermal policies that may be triggered by any combination of signals generated by the sensors 157, 24. For instance, TPM module(s) 101, in some embodiments, may compare operating temperatures measured by sensors 157A with a temperature threshold determined from a proximity signal generated by a sensor associated with sensor module 24 and apply a thermal management policy based on the comparison. In other embodiments, the TPM module(s) 101 may compare a "touch temperature" measurement taken by a sensor 157B and with a temperature threshold determined from a proximity signal generated by a sensor of sensor module 24 and apply a thermal management policy based on the comparison that serves to mitigate thermal energy generation. Notably, the application of thermal management and/or mitigation policies by the TPM module(s) 101 may help a WCD 100 avoid critical temperatures while maintaining a high level of functionality.

Similarly, the PD module(s) 26 may comprise software that is executed by the CPU 110. However, the PD module(s) 26 may also be formed from hardware and/or firmware without departing from the scope of the invention.

Returning to FIG. 2, the touch screen display 132, the video port 138, the USB port 142, the camera 148, the first stereo speaker 154, the second stereo speaker 156, the microphone 160, the FM antenna 164, the stereo headphones 166, the RF switch 170, the RF antenna 172, the keypad 174, the mono headset 176, the vibrator 178, thermal sensors 157B, proximity sensor module 24 and the power supply 180 are external to the on-chip system 102. However, it should be understood that the monitor module 114 may also receive one or more indications or signals from one or more of these external devices by way of the analog signal processor 126 and the CPU 110 to aid in the real time management of the resources operable on the WCD 100. Further, it will be understood that one or more of these devices depicted as external to the on-chip system 102 in the exemplary embodiment of a WCD 100 in FIG. 2 may reside on chip 102 in other exemplary embodiments. The docking station 182 is depicted as being off-chip, however, it will be understood by one of ordinary skill in the art that a docking station 182 may be in communication with the chip 102 only when the WCD 100 is physically received by the docking station 182. Further, as one of ordinary skill in the art will recognize, a docking station 182 may be configured to received a WCD 100 such that one or more external devices such as, but not limited to, a keyboard, monitor, mouse, printer, etc. may be leveraged by the WCD 100 for the benefit of its user.

In a particular aspect, one or more of the method steps described herein may be implemented by executable instructions and parameters stored in the memory 112 that form the one or more TPM module(s) 101 and PD module(s) 26. These instructions that form the TPM module(s) 101 and PD module(s) 26 may be executed by the CPU 110, the analog signal processor 126, or another processor, in addition to the ADC controller 103 to perform the methods described herein. Further, the processors 110, 126, the memory 112, the instructions stored therein, or a combination thereof may serve as a means for performing one or more of the method steps described herein.

Figure 3A:
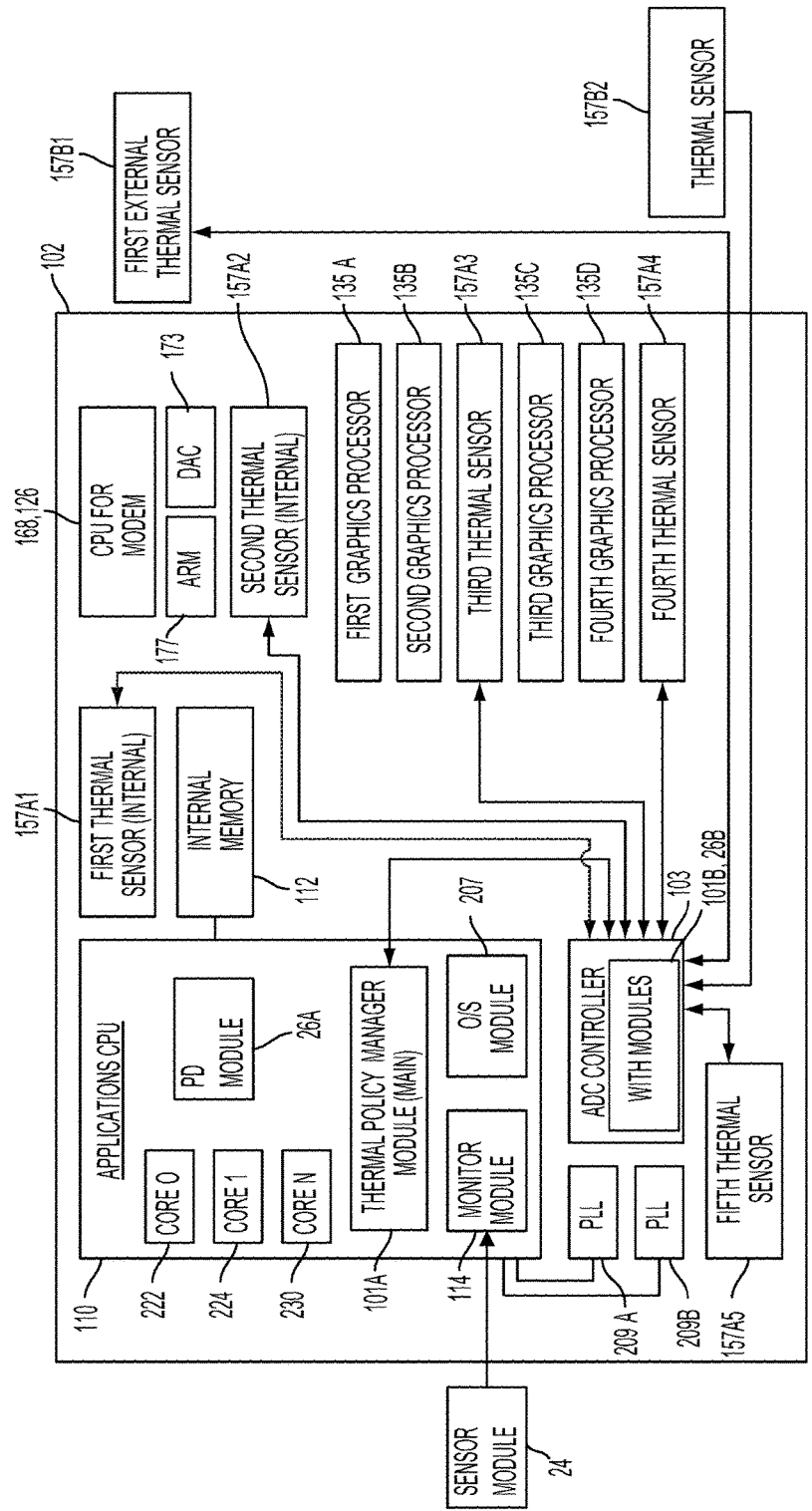
FIG. 3A is a functional block diagram illustrating an exemplary spatial arrangement of hardware for the chip illustrated in FIG. 2.

FIG. 3A is a functional block diagram illustrating an exemplary spatial arrangement of hardware for the chip 102 illustrated in FIG. 2. According to this exemplary embodiment, the applications CPU 110 is positioned on the far left side region of the chip 102 while the modem CPU 168, 126 is positioned on a far right side region of the chip 102. The applications CPU 110 may comprise a multi-core processor that includes a zeroth core 222, a first core 224, and an Nth core 230. The applications CPU 110 may be executing a TPM module 101A and/or PD module 26A (when embodied in software) or it may include a TPM module 101A and/or PD module 26A (when embodied in hardware). The application CPU 110 is further illustrated to include operating system ("O/S") module 207 and a monitor module 114. Further details about the monitor module 114 will be described below in connection with FIG. 3B.

The applications CPU 110 may be coupled to one or more phase locked loops ("PLLs") 209A, 209B, which are positioned adjacent to the applications CPU 110 and in the left side region of the chip 102. Adjacent to the PLLs 209A, 209B and below the applications CPU 110 may comprise an analog-to-digital ("ADC") controller 103 that may include its own thermal policy manager 101B and/or PD module 26B that works in conjunction with the main modules 101A, 26A of the applications CPU 110.

The thermal policy manager 101B of the ADC controller 103 may be responsible for monitoring and tracking multiple thermal sensors 157 that may be provided "on-chip" 102 and "off-chip" 102. The on-chip or internal thermal sensors 157A may be positioned at various locations and associated with thermal aggressor(s) proximal to the locations.

As a non-limiting example, a first internal thermal sensor 157A1 may be positioned in a top center region of the chip 102 between the applications CPU 110 and the modem CPU 168,126 and adjacent to internal memory 112. A second internal thermal sensor 157A2 may be positioned below the modem CPU 168, 126 on a right side region of the chip 102. This second internal thermal sensor 157A2 may also be positioned between an advanced reduced instruction set computer ("RISC") instruction set machine ("ARM") 177 and a first graphics processor 135A. A digital-to-analog controller ("DAC") 173 may be positioned between the second internal thermal sensor 157A2 and the modem CPU 168, 126.

A third internal thermal sensor 157A3 may be positioned between a second graphics processor 135B and a third graphics processor 135C in a far right region of the chip 102. A fourth internal thermal sensor 157A4 may be positioned in a far right region of the chip 102 and beneath a fourth graphics processor 135D. And a fifth internal thermal sensor 157A5 may be positioned in a far left region of the chip 102 and adjacent to the PLLs 209 and ADC controller 103.

One or more external thermal sensors 157B may also be coupled to the ADC controller 103. The first external thermal sensor 157B1 may be positioned off-chip and adjacent to a top right quadrant of the chip 102 that may include the modem CPU 168, 126, the ARM 177, and DAC 173. A second external thermal sensor 157B2 may be positioned off-chip and adjacent to a lower right quadrant of the chip 102 that may include the third and fourth graphics processors 135C, 135D. Notably, one or more of external thermal sensors 157B may be leveraged to indicate the touch temperature of the WCD 100, i.e. the temperature that may be experienced by a user in contact with the WCD 100.

One of ordinary skill in the art will recognize that various other spatial arrangements of the hardware illustrated in FIG. 3A may be provided without departing from the scope of the invention. FIG. 3A illustrates yet one exemplary spatial arrangement and how the main TPM and PD modules 101A, 26A and ADC controller 103 with its TPM and PD modules 101B, 26B may recognize thermal conditions that are a function of the exemplary spatial arrangement illustrated in FIG. 3A, compare temperature thresholds dictated by user proximity states with operating temperatures and/or touch temperatures and apply thermal management policies.

Figure 3B:
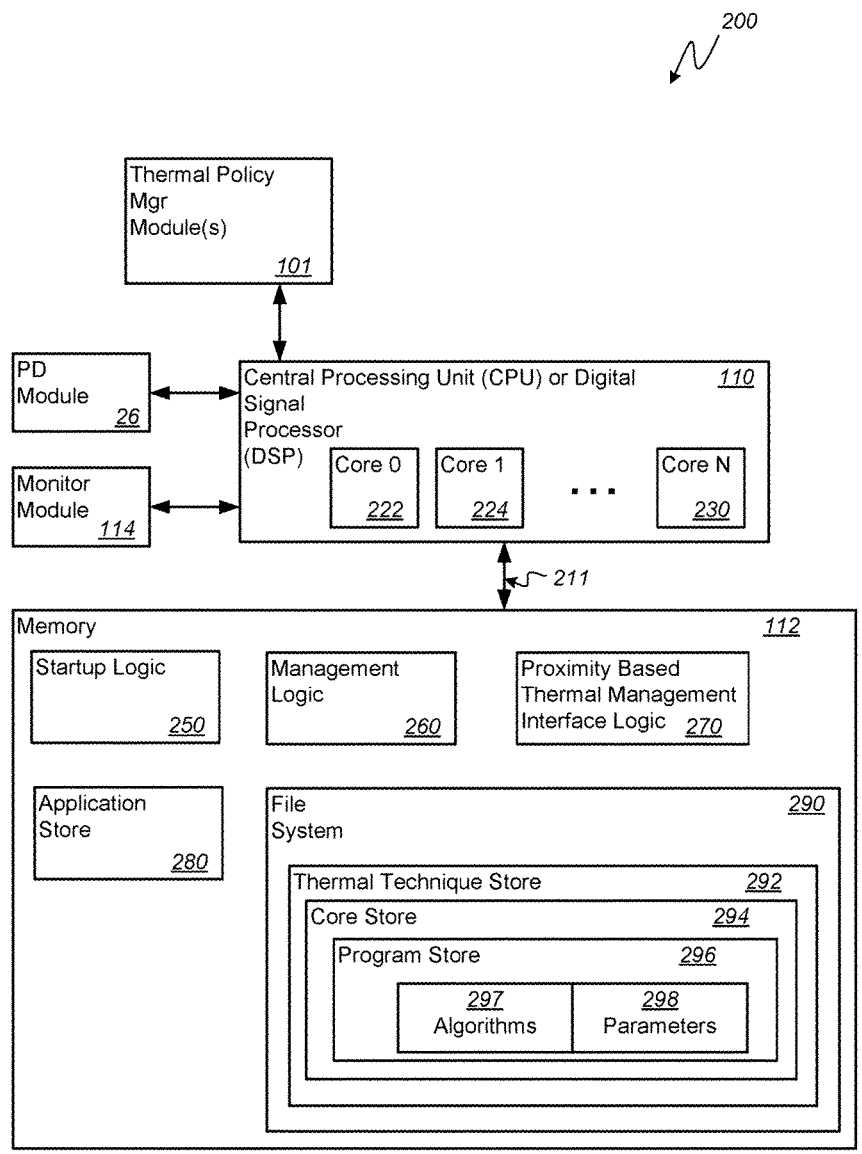
FIG. 3B is a schematic diagram illustrating an exemplary software architecture of the WCD of FIG. 2 for proximity based thermal management.

FIG. 3B is a schematic diagram illustrating an exemplary software architecture of the WCD 100 of FIG. 2 for proximity based thermal management. The exemplary software architecture shown in FIG. 3B may be used for supporting application of thermal management policies based on temperature thresholds dictated by the recognition of WCD 100 proximity, or lack thereof, to a user. Any number of algorithms may form or be part of at least one thermal management policy that may be applied by the thermal policy manager 101 when certain thermal conditions are met.

As illustrated in FIG. 3B, the CPU or digital signal processor 110 is coupled to the memory 112 via a bus 211. The CPU 110, as noted above, is a multiple-core processor having N core processors. That is, the CPU 110 includes a first core 222, a second core 224, and an $N^{th}$ core 230. As is known to one of ordinary skill in the art, each of the first core 222, the second core 224 and the $N^{th}$ core 230 are available for supporting a dedicated application or program. Alternatively, one or more applications or programs can be distributed for processing across two or more of the available cores.

The CPU 110 may receive commands from the TPM module(s) 101 that may comprise software and/or hardware. If embodied as software, the TPM module 101 comprises instructions that are executed by the CPU 110 that issues commands to other application programs being executed by the CPU 110 and other processors.

The first core 222, the second core 224 through to the Nth core 230 of the CPU 110 may be integrated on a single integrated circuit die, or they may be integrated or coupled on separate dies in a multiple-circuit package. Designers may couple the first core 222, the second core 224 through to the $N^{th}$ core 230 via one or more shared caches and they may implement message or instruction passing via network topologies such as bus, ring, mesh and crossbar topologies.

Bus 211 may include multiple communication paths via one or more wired or wireless connections, as is known in the art. The bus 211 may have additional elements, which are omitted for simplicity, such as controllers, buffers (caches), drivers, repeaters, and receivers, to enable communications. Further, the bus 211 may include address, control, and/or data connections to enable appropriate communications among the aforementioned components.

When the logic used by the WCD 100 is implemented in software, as is shown in FIG. 3B, it should be noted that one or more of startup logic 250, management logic 260, proximity based thermal management interface logic 270, applications in application store 280 and portions of the file system 290 may be stored on any computer-readable medium for use by, or in connection with, any computer-related system or method.

In the context of this document, a computer-readable medium is an electronic, magnetic, optical, or other physical device or means that can contain or store a computer program and data for use by or in connection with a computer-related system or method. The various logic elements and data stores may be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

The computer-readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random-access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, for instance via optical scanning of the paper or other medium, then compiled, interpreted or otherwise processed in a suitable manner if necessary, and then stored in a computer memory.

In an alternative embodiment, where one or more of the startup logic 250, management logic 260 and perhaps the proximity based thermal management interface logic 270 are implemented in hardware, the various logic may be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The memory 112 is a non-volatile data storage device such as a flash memory or a solid-state memory device. Although depicted as a single device, the memory 112 may be a distributed memory device with separate data stores coupled to the digital signal processor.

The startup logic 250 includes one or more executable instructions for selectively identifying, loading, and executing a select program for managing or controlling the performance of one or more of the available cores such as the first core 222, the second core 224 through to the $N^{th}$ core 230. The startup logic 250 may identify, load and execute a select program based on the comparison, by the TPM module 101, of various temperature measurements with threshold temperature settings associated with a proximity state. An exemplary select program can be found in the program store 296 of the embedded file system 290 and is defined by a specific combination of a performance scaling algorithm 297 and a set of parameters 298. The exemplary select program, when executed by one or more of the core processors in the CPU 110, may operate in accordance with one or more signals provided by the monitor module 114 in combination with control signals provided by the one or more TPM module(s) 101 to scale the performance of the respective processor core "up" or "down." In this regard, the monitor module 114 may provide one or more indicators of events, processes, applications, resource status conditions, elapsed time, as well as temperature as received from the TPM module 101.

The management logic 260 includes one or more executable instructions for terminating a thermal management program on one or more of the respective processor cores, as well as selectively identifying, loading, and executing a more suitable replacement program for managing or controlling the performance of one or more of the available cores. The management logic 260 is arranged to perform these functions at run time or while the WCD 100 is powered and in use by an operator of the device. A replacement program can be found in the program store 296 of the embedded file system 290 and, in some embodiments, may be defined by a specific combination of a performance scaling algorithm 297 and a set of parameters 298.

The replacement program, when executed by one or more of the core processors in the digital signal processor, may operate in accordance with one or more signals provided by the monitor module 114 or one or more signals provided on the respective control inputs of the various processor cores to scale the performance of the respective processor core. In this regard, the monitor module 114 may provide one or more indicators of events, processes, applications, resource status conditions, elapsed time, temperature, etc in response to control signals originating from the TPM 101.

The interface logic 270 includes one or more executable instructions for presenting, managing and interacting with external inputs to observe, configure, or otherwise update information stored in the embedded file system 290. In one embodiment, the interface logic 270 may operate in conjunction with manufacturer inputs received via the USB port 142 or wirelessly depending on embodiment of the WCD 100. These inputs may include one or more programs to be deleted from or added to the program store 296. Alternatively, the inputs may include edits or changes to one or more of the programs in the program store 296. Moreover, the inputs may identify one or more changes to, or entire replacements of one or both of the startup logic 250 and the management logic 260. By way of example, the inputs may include a change to the management logic 260 that instructs the WCD 100 to suspend all performance scaling in the RF transceiver 168 (see FIG. 2) when the received signal power falls below an identified threshold.

The interface logic 270 enables a manufacturer to controllably configure and adjust an end user's experience under defined operating conditions on the WCD 100. When the memory 112 is a flash memory, one or more of the startup logic 250, the management logic 260, the interface logic 270, the application programs in the application store 280 or information in the embedded file system 290 can be edited, replaced, or otherwise modified. In some embodiments, the interface logic 270 may permit an end user or operator of the WCD 100 to search, locate, modify or replace the startup logic 250, the management logic 260, applications in the application store 280 and information in the embedded file system 290. The operator may use the resulting interface to make changes that will be implemented upon the next startup of the WCD 100. Alternatively, the operator may use the resulting interface to make changes that are implemented during run time.

The embedded file system 290 includes a hierarchically arranged thermal technique store 292. In this regard, the file system 290 may include a reserved section of its total file system capacity for the storage of information for the configuration and management of the various parameters 298 and thermal management algorithms 297 used by the WCD 100. As shown in FIG. 3B, the store 292 includes a core store 294, which includes a program store 296, which includes one or more thermal management programs.

Figure 4:
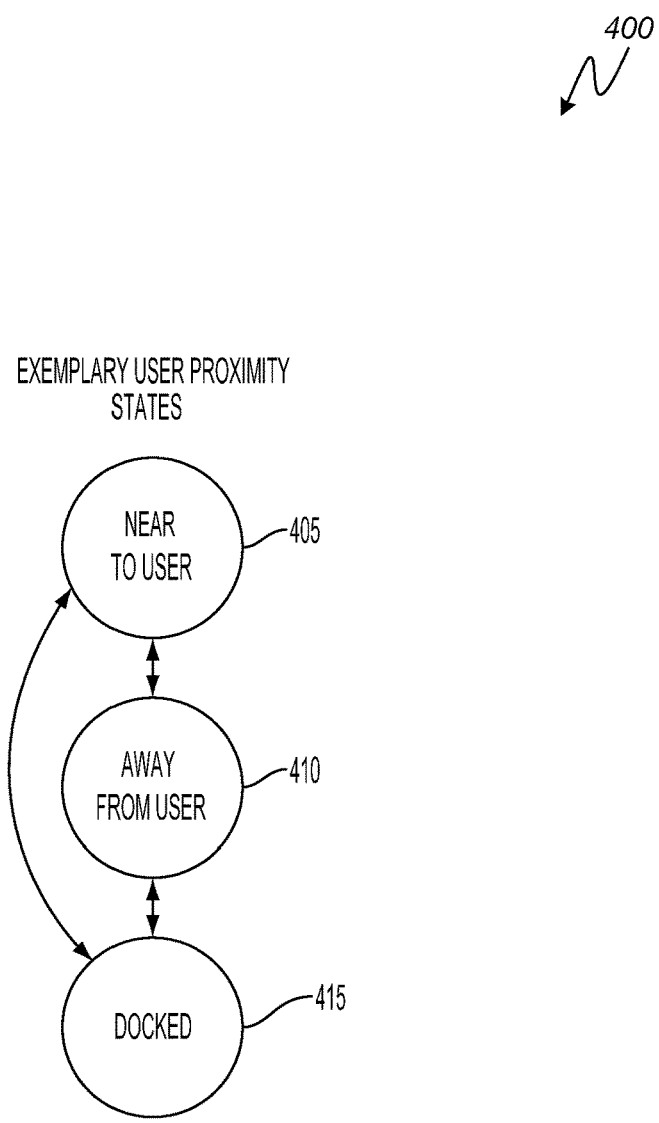
FIG. 4 is a is an exemplary state diagram that illustrates various proximity based policy states that may trigger temperature thresholds set by the proximity determination module in the WCD of FIG. 1.

FIG. 4 is an exemplary state diagram 400 that illustrates various proximity based policy states (I.e., user proximity states) 405, 410 and 415 that may trigger temperature thresholds set by the proximity determination module 26 in the WCD of FIG. 1. The first policy state 405 may comprise a "near to user" state in which the PD module 26 recognizes or concludes from the sensor module 24 that the WCD 100 is near, or in contact with, a user. Notably, in the near to user state 405, the touch temperature of the WCD 100, as may be indicated by an off-chip sensor 157B, is leveraged by the thermal policy manager 101 to determine thermal management policies suitably for maintaining the touch temperature below a predefined temperature threshold. In some embodiments, the touch temperature threshold may be the default temperature threshold that is leveraged by the TPM module 101 to manage thermal energy generation. The TPM 101 may monitor any, or a combination of, thermal sensors 157 to measure or derive the touch temperature of WCD 100 prior to applying, maintaining or terminating a thermal management policy.

In this exemplary near to user state 405, the WCD 100 is usually not in any danger or risk of reaching critical temperatures that may cause failure of any of the hardware and/or software components because the touch temperature is commonly significantly less than the operating temperature limits of the components within WCD 100. In this exemplary state, the thermal sensors 157 may be detecting or tracking temperatures that indicate a touch temperature at or below about 20° C. above ambient. However, one of ordinary skill in the art will recognize that other temperature ranges may be established for the near to user state 405 without departing from the scope of the invention.

The second policy state 410 may comprise an "away from user" state 410 in which the PD module 26 recognizes from the sensor module 24 that the WCD 100 is not proximal to a user. Notably, in the away from user state 410, temperatures associated with one or more processing components of the WCD 100, as may be indicated by an on-chip sensor 157A or correlated with a measurement by an off-chip sensor 157B, is leveraged by the thermal policy manager 101 to determine thermal management policies suitable for optimizing processing performance without exceeding operating temperature thresholds of the various processing components. Advantageously, in the away from user state 410, the touch temperature of the WCD 100 may be allowed to exceed the temperature threshold described above relative to state 405, as the WCD 100 is not in immediate proximity to a user. As such, the TPM module 101 may implement thermal management policies that allow the various processing components to increase performance, thereby increasing QoS, even though thermal energy generation associated with the increased performance may cause the touch temperature to exceed its normal target threshold.

It is envisioned that, in some embodiments, the away from user state 410 may include a temperature threshold that exceeds the default touch temperature threshold described above but is less than the maximum operating temperature of the various processing components. In this way, subject to the temperature threshold set by the PD module 26 when the WCD 100 is in the policy state 410, the TPM module 101 may apply thermal management policies that provide for increased processing performance without dissipating thermal energy at a rate that may cause the touch temperature to become unbearable should the WCD 100 reenter policy state 405 when a user "puts it on." That is, in policy state 410, the default touch temperature threshold may be adjusted by the PD module 26 to allow for increased processing performance without causing the WCD 100 to become so hot that thermal energy can't be quickly dissipated upon reentry into the near to user policy state 405.

The temperature threshold set by the PD module 26 when the WCD 100 is recognized to be in policy state 410 may be associated with an adjusted touch temperature or, alternatively, may be associated with an acceptable operating temperature of one or more processing components. In either case, the TPM module 101 may leverage any, or a combination of, measurements taken by sensors 157 prior to applying, maintaining or terminating a thermal management policy based on the temperature threshold set by PD module 26.

As will be understood by one of ordinary skill in the art, this exemplary away from user state 410 may be reached or entered into by the thermal policy manager 101 when a change of user proximity has been detected relative to states 405 and 415. In the second, away from user state 410 the TPM module 101 may request or it may actually perform one or more thermal management techniques in order to increase the processing performance, and consequently the temperature as well, of the WCD 100. In this particular state 410, the thermal policy manager 101 is designed to implement or request thermal mitigation techniques that may significantly increase the quality of service provided by the WCD 100 to a user, at the expense of increasing the touch temperature of the WCD 100. The temperature range for the operating temperature of one or more processing components in this second, away from user proximity state 410 may comprise a range between about 25° C. above ambient to about 40° C. above ambient. One of ordinary skill in the art will recognize, however, that other temperature ranges may be established for the policy state 410 and are within the scope of the invention.

The third policy state 415 may comprise a "docked" state in which the WCD 100 has been received by a docking station 182 or other hardware device configured to allow the WCD 100 to communicate with one or more external devices such as, but not limited to, a keyboard, a monitor, a mouse, a printer, etc. In some embodiments, a docking station or other peripheral device may include mechanical interface aspects that contribute to the efficiency of thermal energy dissipation from the WCD 100. Notably, when a WCD 100 is docked the PD module 26 may recognize that the WCD 100 is not only physically separated from a user but also received by the docking station and unlikely to be physically contacted by a user. As such, when the WCD 100 is recognized as being in the docked state 415, the PD module 26 may set temperature thresholds such that the TPM module 101 may apply thermal management policies that allow the processing components 110 and/or other components of the WCD 100 to run at high rates of power consumption. Advantageously, because the WCD 100 is in communication with a docking station 182, the PD module 26 may recognize that performance efficiency is a more significant factor for user experience than touch temperature and, accordingly, set temperature thresholds that trigger the TPM module 101 to implement thermal management policies geared for optimizing WCD performance at the expense of thermal energy generation. The temperature range for threshold temperatures of various components when the WCD 100 is in this third, docked state 415 may comprise a range limited only by a maximum temperature specified for a brief touch (e.g., 95° C. for plastic surfaces per UL 60950), although other limits are envisioned to be within the scope of the disclosure.

As one of ordinary skill in the art will recognize, any of the various user proximity policy states may be initiated based upon the change in proximity to a user, as detected by the sensor module 24 and recognized by the PD module 26. For example, as the arrows in this diagram illustrate, each policy state may be initiated in sequence or they can be initiated out of sequence depending upon the change in proximity to a user.

FIG. 5 is a diagram illustrating exemplary thermal management policies and associated conditions that may be leveraged by the thermal policy manager module 101 in FIG. 1 and are dependent upon a particular user proximity state illustrated in FIG. 4. As noted previously, the first proximity state 405 may comprise a "near to user" state in which the thermal policy manager 101 being executed by the CPU 110 and partially by the ADC controller 103 may monitor, poll, or receive one or more status reports on temperature from one or more thermal sensors 157, compare the status reports to a threshold temperature associated with an acceptable touch temperature of the device, and apply appropriate thermal management policies to maintain the touch temperature below the threshold. In this first policy state 405, the PD module 26 may have received a signal(s) from the sensor module 24 indicating that the WCD 100 is proximal to a user. Because the WCD 100 is near the user, the touch temperature threshold may be a primary determinant of user experience and, as such, the TPM 101 may implement thermal mitigation techniques that sacrifice QoS in favor of mitigating thermal energy generation.

The second proximity state 410 may comprise an "away from user" state in which the thermal policy manager 101 being executed by the CPU 110 and partially by the ADC controller 103 may monitor, poll, or receive one or more status reports on temperature from one or more thermal sensors 157, compare the status reports to a threshold temperature associated with an increased touch temperature of the device and apply appropriate thermal management policies to optimize performance without exceeding the adjusted touch temperature threshold. In this second policy state 410, the PD module 26 may have received a signal from the sensor module 24 indicating that the WCD 100 is not proximal to a user. Because the WCD 100 is not near the user, the touch temperature threshold may be increased such that the primary determinant of user experience is the QoS subject to a modest increase in touch temperature. As such, the TPM 101 may implement thermal management techniques that increase the performance level of one or more components at the expense of increased thermal energy generation. Notably, in some embodiments, the increased touch temperature may be determined based on a level that allows for increased performance without generating so much thermal energy that the WCD 100 cannot dissipate energy at a reasonable rate for reentry into the first policy state.

The third proximity state 415 may comprise a "docked" state in which the thermal policy manager 101 being executed by the CPU 110 and partially by the ADC controller 103 may monitor, poll, or receive one or more status reports on temperature from one or more thermal sensors 157, compare the status reports to a threshold temperature associated with temperature operating limits of one or more components within the WCD 100, and apply appropriate thermal management policies to optimize performance without detrimentally effecting the WCD 100. In this third policy state 415, the PD module 26 may have received a signal from the sensor module 24 indicating that the WCD 100 is not proximal to a user and/or confirmation that the WCD 100 has been received by an external docking device. Because the WCD 100 is not near the user and has been received into a docking device for the full leveraging of its performance capabilities, the touch temperature threshold may not be a significant driver of user experience. Rather, in the docked state, the primary driver of user experience may be the QoS subject only to operating temperatures that could damage the WCD 100. As such, the TPM 101 may implement thermal management techniques that substantially increase component performance at the expense of thermal energy generation.

Figure 6:
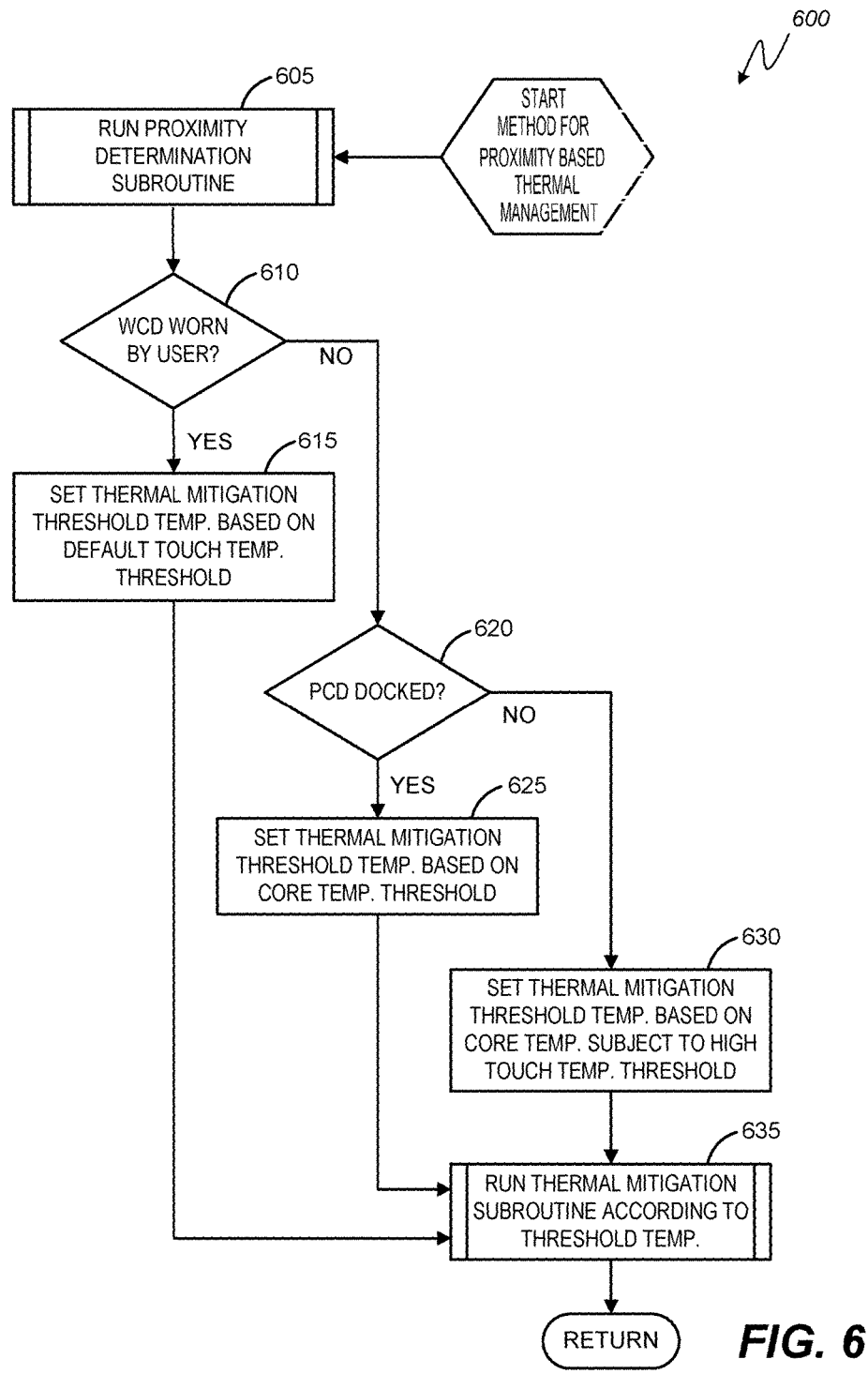
FIG. 6 is a logical flowchart illustrating a method for managing one or more thermal policies based on an indication of user proximity.

FIG. 6 is a logical flowchart illustrating a method 600 for managing one or more thermal policies based on an indication of user proximity. The method 600 leverages user proximity calculations as a trigger for applying thermal management policies within a WCD 100.

Figure 7:
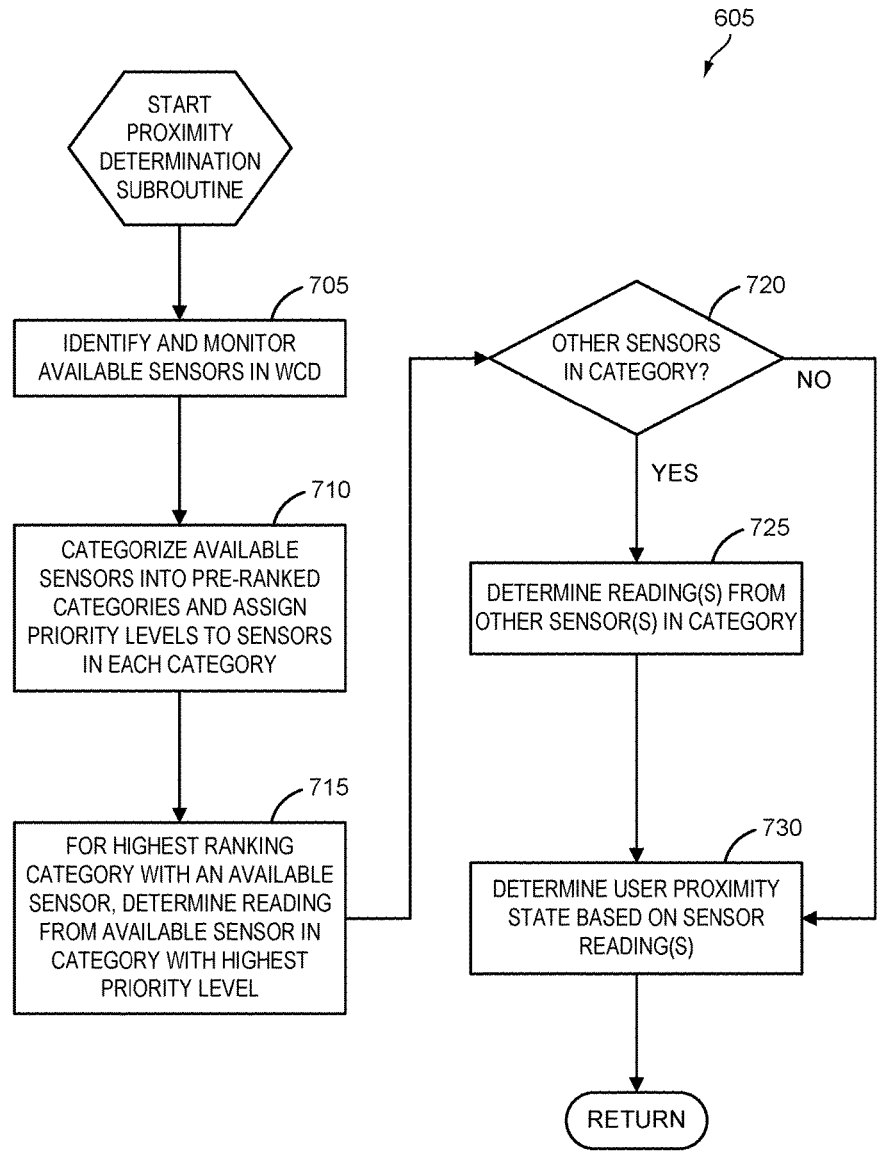
FIG. 7 is a logical flowchart illustrating a sub-method or subroutine for determining proximity of a WCD to a user.
Figure 8:
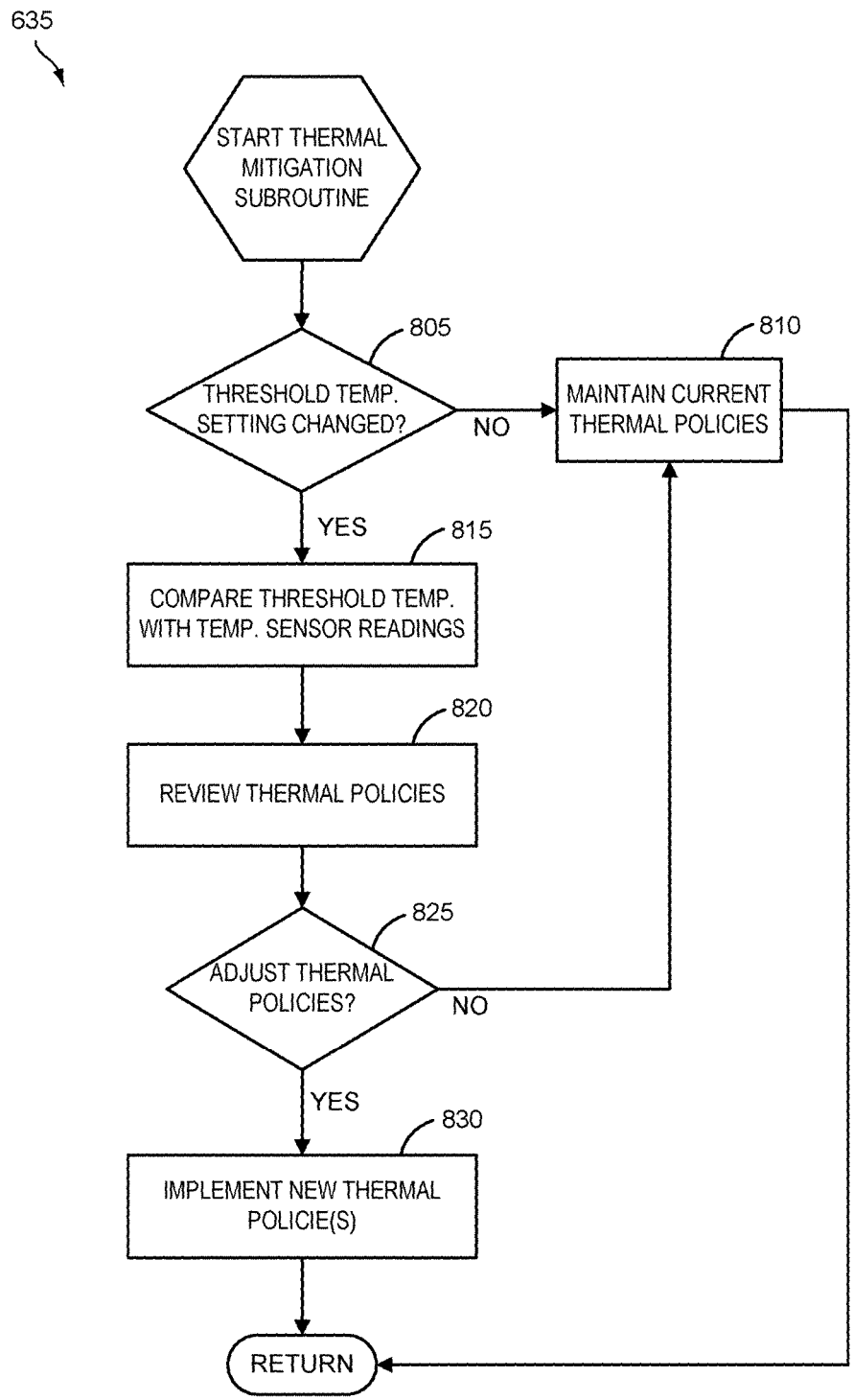
FIG. 8 is a logical flowchart illustrating a sub-method or subroutine for applying thermal management policies.

Method 600 of FIG. 6 starts with subroutine block 605 for generating a determination of a user proximity state (more details regarding subroutine 605 are shown and described relative to the FIG. 7 illustration). With an output generated from subroutine 605, the method proceeds to a first decision block 610 in which the PD module 26 may receive data representative of user proximity, or lack thereof, to the WCD 100. As has been described above, sensor readings generated by sensors associated with a sensor module 24 may be monitored by a monitor module 114 for signals useful in calculating, determining or inferring user proximity to the WCD 100. The monitor module 114 may be in communication with the PD module 26. If it is determined at decision block 610 that the WCD 100 is proximal to a user, the "yes" branch is followed to block 615. At block 615, the PD module 26 may set, or leave unchanged, a temperature threshold at a level associated with an acceptable touch temperature of the WCD 100. In such a case, at block 635 the TPM module 101 may apply thermal mitigation techniques operable to maintain the touch temperature of the WCD 100 below the acceptable threshold (more details regarding subroutine 635 are shown and described relative to the FIG. 8 illustration).

If it is determined at decision block 610 that the WCD 100 is not proximal to a user, then the "no" branch is followed to decision block 620. At decision block 620, the PD module 26 may determine if the WCD 100 is away from a user and/or received in a docking device. If it is determined that the WCD 100 is away from a user but not received into a docking device, then the "no" branch is followed to block 630. At block 630 the PD module 26 may set a temperature threshold, for triggering thermal management policies, that allows one or more components to generate thermal energy at a rate that raises the touch temperature of the WCD 100 above the default threshold described above relative to block 615. Notably, at block 630 of the method, the temperature threshold set by the PD module 26 may be subject to a condition that the touch temperature threshold does not exceed the default touch temperature threshold by such an amount that the WCD 100 cannot quickly cool to below the default touch temperature setting. At subroutine block 635, the TPM module 101 may apply thermal mitigation techniques operable to maintain the operating temperature of the WCD 100 below the acceptable threshold.

If at decision block 620, the PD module 26 determines that the WCD 100 is not only away from the user but also received into a docking device for driving one or more external devices, the "yes" branch is followed to block 625. At block 625, the PD module 26 may set the temperature threshold for application of thermal management policies at a relatively high operating temperature. Notably, when the WCD 100 is determined to be in a docked state, certain embodiments may assume that the touch temperature of the WCD 100 is not a primary driver of user experience and, as such, set a temperature threshold that allows the performance efficiency of one or more components within the WCD 100 to run at a rate that generates high levels of thermal energy. In some embodiments, it is envisioned that thermal management techniques implemented at block 635 may operate only to mitigate thermal energy generation that could potentially damage the WCD 100 while in other embodiments the temperature threshold set by the PD module 26 when the WCD 100 is docked may still be subject to a maximum touch temperature threshold.

Concerning the application of thermal management techniques by the TPM module 101, one of ordinary skill in the art will recognize that systems and methods for triggering thermal management policies based on proximity and temperature measurements are not limited by the particular thermal management techniques that may or may not be triggered. Even so, thermal mitigation techniques that may be initiated by one or more embodiments include, but not limited to, (1) load scaling and/or (2) load dynamic scaling; (3) spatial load shifting; and (4) process load reallocation. Generally, thermal management techniques that include load scaling may comprise adjusting or "scaling" the maximum clock frequency allowed in a dynamic voltage and frequency scaling ("DVFS") algorithm. Advantageously, such an adjustment may limit the maximum heat dissipation. Thermal management techniques that include spatial load shifting and/or load reallocation include algorithms for distributing workloads within a given processing core or across multiple processing cores. In this way, thermal energy generation and dissipation may be managed by distributing the workload across a larger processing area, processing the workload in processing capacity associated with higher or lower power densities relative to initial allocation, or leveraging underutilized processing components to perform as heat sinks.

FIG. 7 is a logical flowchart illustrating a sub-method or subroutine 605 for determining proximity of a WCD 100 to a user. Beginning at block 705, all available or eligible sensors in sensor module 24 may be identified by the monitor module 114 and/or the PD module 26. As described above, in WCDs 100, any number of sensors may be included for primary purposes other than user proximity sensing such as, but not limited to, sensing or measuring heart rate, pulse, blood oxygen saturation, bio-impedance, global positioning coordinates, rotational motion (gyroscope), acceleration force (accelerometer), temperature, pressure, capacitance, resistance, motion, specific absorption rate, light, etc. Embodiments of the solution, advantageously, leverage readings from sensors in sensor module 24 to deduce, infer, or determine user proximity states.

Returning to the subroutine 605, after available sensors are identified, the subroutine continues to block 710. At block 710, the PD module 26 may categorize the identified sensors into pre-ranked categories and, for each sensor in a category, assign a priority level. The purpose of categorizing and ranking the various sensors identified at block 705 may be to, among other reasons, recognize those sensor readings that, individually or combination, may be dispositive of a user proximity state. For example, if at block 705 a pulse oximeter sensor is recognized, generation of a reading by the sensor that is indicative of viable blood oxygen level may be leveraged by embodiments of the solution to conclude that the WCD 100 is being worn by a user (I.e., a "near to user" state 405). As another example, if at block 705 a changing GPS signal is recognized (thus indicating that the WCD 100 is moving and therefore may be in a "near to user" state 405) but a sensor for measuring acceleration force (i.e., an accelerometer) is generating a signal from which it may be concluded that the WCD 100 is not moving in a manner consistent with being worn, embodiments of the solution may consider the readings in combination to conclude that the WCD 100 is not being worn by a user (I.e., maybe it's in a glove compartment of a slow moving car or a cup holder of a golf cart).

Returning to the subroutine 605, at block 715 the PD module 26 may consider the sensor with the highest priority in the highest ranking category (I.e., that sensor or sensors with the most relevant or reliable data for determining user proximity). Next, at decision block 720 if there are no other sensors in the highest ranking category, the subroutine 605 may follow the "no" branch to block 730 and the PD module 26 may leverage the reading from the highest priority sensor to determine a user proximity state. Notably, if the single sensor with the highest priority in the highest category is not dispositive of a user proximity state, the subroutine may loop back through to consider sensors in less highly ranked categories in combination with the highest priority sensor, the combination of which may be used by the PD module 26 to determine a likely user proximity state. It is envisioned that, in some embodiments of the solution, if sensors of equal or comparable priority generate signal readings that, individually considered, would cause a PD module 26 to arrive at different user proximity determinations, then the embodiment may conclude that the likely user proximity state is the state associated with the most stringent or lowest thermal thresholds.

Returning to decision block 720, if multiple sensors are categorized into a same category, the subroutine may follow the "yes" branch to block 725 and readings from the other sensors read and considered. At block 730, a user proximity state may be concluded in view of the various readings generated by the sensor(s) individually and/or in combination.

Regarding the ranking of sensor categories, it is envisioned that some embodiments of the solution may rank in the following exemplary and non-limiting manner. A highest ranked category may be associated with health tracking sensors such as, but not limited to, heart rate monitors, pulse monitor, $O^2$ sensors, etc. A second highest ranked category may be associated with touch sensors such as, but not limited to, bio-impedance sensors, capacitive sensors, resistive sensors, etc. A third highest ranked category may be associated with temperature sensors (ambient and/or on-chip sensors) the readings from which may be used in combination with non-temperature sensor readings to improve user proximity state determination. A fourth highest ranked category may be reserved for pressure sensors (it is envisioned that pressure sensors may be categorized in a relatively higher ranked category if the WCD 100 is in the form of a device typically worn tightly by a user such as, but not limited to, a VR/AR headset as opposed to a device typically worn loosely such as a smartwatch or fitness tracker). A fifth highest ranked category may be associated with location and/or orientation based sensors such as, but not limited to, accelerometers, gyroscopes, GPS, etc. due to the fact that motion, in and of itself, may be attributable to some use case other than the WCD 100 being worn by a user. It is envisioned, however, that certain embodiments of the solution may be configured to analyze a motion-based reading in more detail such as to determine whether the motion is consistent with a WCD 100 being worn by a user and, in such embodiments, location and/or orientation based sensors may be higher categorized sensors (e.g., an embodiment configured to recognize from an accelerometer reading that a wrist-worn WCD 100 is accelerating and decelerating according to a pattern consistent with a user swinging his arms back and forth while running may assign a relatively high priority to an accelerometer sensor reading when determining a user proximity state). Logical categorizations, prioritizations and combinations of sensor readings that may be leveraged by an embodiment of the solution to determine, with suitably high probability of success, a user proximity state will occur to those of skill in the art reviewing this disclosure.

FIG. 8 is a logical flowchart illustrating an exemplary, non-limiting sub-method or subroutine 635 for applying thermal management policies. The method 635 of FIG. 8 starts with decision block 805. At block 805, the TPM module 101 may determine whether the PD module 26 has recognized a user proximity state of the WCD 100 from sensor readings taken from sensor module 24 and, in response, changed the threshold temperature for triggering thermal management policies. Notably, as has been described throughout this disclosure, the PD module 26 may not only change or set a threshold temperature, but may also change or determine an aspect within the WCD 100 that is associated with the threshold temperature. For instance, as has been described above, the threshold temperature determined by the PD module 26, and used by the TPM module 101 to trigger thermal management policy, may be associated with any number of aspects within the WCD 100 including, but not limited to, a processing component (i.e., operating temperature of the component), the external temperature of the WCD 100 (i.e., the touch temperature of the device) or a cascaded logic that includes a first threshold temperature measured by a first sensor subject to a second threshold temperature measured by a second sensor.

If the TPM module 101 determines at decision block 805 that the threshold temperature has not been changed by the PD module 26, then the presently implemented thermal management policies may be maintained by the TPM module 101. If, however, at decision block 805 the TPM module 101 recognizes a change in the temperature threshold and/or the sensor that is monitored for the temperature threshold, the "yes" branch is followed to block 815. At block 815, the TPM module 101 may compare the newly set temperature threshold to the actual temperature measured at an associated sensor such as, for example, sensors 157A or 157B. Based on the comparison, the TPM module 101 may review the currently implemented thermal management policies, if any, at block 820 and decide at decision block 825 whether the currently implemented thermal management policies require adjustment. If at decision block 825 the TPM module 101 determines that no adjustment or modification of thermal management policies is warranted in light of the block 815 comparison, the "no" branch is followed back to block 810 and the current policies are maintained. If, however, at decision block 825 the TPM module 101 determines that a change or modification of thermal management policies is warranted, the "yes" branch is followed to block 830 and the TPM module 101 may elect to implement one or more alternative thermal management techniques.

Certain steps in the processes or process flows described in this specification naturally precede others for the invention to function as described. However, the invention is not limited to the order of the steps described if such order or sequence does not alter the functionality of the invention. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary method.

Additionally, one of ordinary skill in programming is able to write computer code or identify appropriate hardware and/or circuits to implement the disclosed invention without difficulty based on the flow charts and associated description in this specification, for example. Therefore, disclosure of a particular set of program code instructions or detailed hardware devices is not considered necessary for an adequate understanding of how to make and use the invention. The inventive functionality of the claimed computer implemented processes is explained in more detail in the above description and in conjunction with the drawings, which may illustrate various process flows.

In one or more exemplary aspects, the functions described may be implemented in hardware, software, firmware, or any combination thereof. If implemented in software, the functions may be stored on or transmitted as one or more instructions or code on a computer-readable medium. Computer-readable media include both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a coaxial cable, fiber optic cable, twisted pair, digital subscriber line ("DSL"), or wireless technologies such as infrared, radio, and microwave, then the coaxial cable, fiber optic cable, twisted pair, DSL, or wireless technologies such as infrared, radio, and microwave are included in the definition of medium.

Disk and disc, as used herein, includes compact disc ("CD"), laser disc, optical disc, digital versatile disc ("DVD"), floppy disk and blu-ray disc where disks usually reproduce data magnetically, while discs reproduce data optically with lasers. Combinations of the above should also be included within the scope of computer-readable media.

Therefore, although selected aspects have been illustrated and described in detail, it will be understood that various substitutions and alterations may be made therein without departing from the spirit and scope of the present invention, as defined by the following claims.

What is claimed is:

1. A method for managing thermal energy generation in a wearable computing device ("WCD"), the method comprising:
   monitoring one or more health-tracking signals from one or more health-tracking sensors of the WCD;
   based on the monitored one or more health-tracking signals, both providing corresponding health-tracking information and determining a user proximity state for the WCD;
   based on the user proximity state, setting a first temperature threshold for a thermal management policy; and
   comparing the first temperature threshold with a temperature measurement received from a first temperature sensor to manage thermal energy generation in the WCD.

2. The method of claim 1, further comprising:
if the temperature measurement received from the first temperature sensor is less than the first temperature threshold, then maintaining a currently implemented thermal management policy.

3. The method of claim 1, further comprising:
if the temperature measurement received from the first temperature sensor is greater than the first temperature threshold, then modifying a currently implemented thermal management policy.

4. The method of claim 1, wherein the health-tracking sensors comprise at least one of a heart-rate monitor, a pulse monitor, and an O2 sensor.

5. The method of claim 1, wherein the determined user proximity state defines that the WCD is proximal to a user and the first temperature threshold is associated with the touch temperature of the WCD.

6. The method of claim 1, wherein the determined user proximity state defines that the WCD is in a docked state and not physically proximal to a user.

7. The method of claim 1, wherein the determined user proximity state defines that the WCD is not physically proximal to a user and the first temperature threshold is associated with the operating temperature of a processing component in the WCD.

8. The method of claim 7, further comprising:
setting a second temperature threshold that is associated with a second temperature sensor in the WCD;
comparing the second temperature threshold with a temperature measurement received from the second temperature sensor; and
based on the comparison of the first temperature threshold with the temperature measurement received from the first temperature sensor, modifying a currently implemented thermal management policy, wherein the modified thermal management policy prevents the second temperature sensor measurement from exceeding the second temperature sensor threshold.

9. The method of claim 1, further comprising also using one or more monitored signals from one or more of a bio-impedance sensor, a gyroscope, an accelerometer, a temperature sensor, a pressure sensor, a capacitive sensor, a resistive sensor and a light sensor of the WCD to determine the user proximity state for the WCD.

10. The method of claim 7, wherein the first temperature threshold is associated with a maximum operating temperature of the processing component.

11. A computer system for managing thermal energy generation in a wearable computing device ("WCD"), the system comprising:
a proximity determination ("PD") module programmed to:
monitor one or more health-tracking signals from one or more health-tracking sensors of the WCD;
based on the monitored one or more health-tracking signals, both provide corresponding health-tracking information and determine a user proximity state for the WCD; and
based on the user proximity state, set a first temperature threshold for a thermal management policy; and
a thermal policy manager ("TPM") module programmed to:
compare the first temperature threshold with a temperature measurement received from a first temperature sensor; and
based on the comparison, manage thermal energy generation in the WCD.

12. The computer system of claim 11, wherein the TPM module is further programmed to:
if the temperature measurement received from the first temperature sensor is less than the first temperature threshold, then maintaining a currently implemented thermal management policy.

13. The computer system of claim 11, wherein the TPM module is further programmed to:
if the temperature measurement received from the first temperature sensor is greater than the first temperature threshold, then modifying a currently implemented thermal management policy.

14. The computer system of claim 11, wherein the health-tracking sensors comprise at least one of a heart-rate monitor, a pulse monitor, and an O2 sensor.

15. The computer system of claim 11, wherein the determined user proximity state defines that the WCD is proximal to a user and the first temperature threshold is associated with the touch temperature of the WCD.

16. The computer system of claim 11, wherein the determined user proximity state defines that the WCD is in a docked state and not physically proximal to a user.

17. The computer system of claim 11, wherein the determined user proximity state defines that the WCD is not physically proximal to a user and the first temperature threshold is associated with the operating temperature of a processing component in the WCD.

18. The computer system of claim 17, wherein:
the PD module is further programmed to:
set a second temperature threshold that is associated with a second temperature sensor in the WCD; and
the TPM module is further programmed to:
compare the second temperature threshold with a temperature measurement received from the second temperature sensor; and
based on the comparison of the first temperature threshold with the temperature measurement received from the first temperature sensor, modify a currently implemented thermal management policy, wherein the modified thermal management policy prevents the second temperature sensor measurement from exceeding the second temperature sensor threshold.

19. The computer system of claim 11, wherein the PD module is further programmed to use one or more monitored signals from one or more of a bio-impedance sensor, a gyroscope, an accelerometer, a temperature sensor, a pressure sensor, a capacitive sensor, a resistive sensor and a light sensor of the WCD to determine the user proximity state for the WCD.

20. The computer system of claim 17, wherein the first temperature threshold is associated with a maximum operating temperature of the processing component.

21. A computer system for managing thermal energy generation in a wearable computing device, the system comprising:
means for monitoring one or more health-tracking signals from one or more health-tracking sensors of the WCD;
means for, based on the monitored one or more health-tracking signals, both providing corresponding health-tracking information and determining a user proximity state for the WCD;
means for, based on the user proximity state, setting a first temperature threshold for a thermal management policy; and means for comparing the first temperature threshold with a temperature measurement received from the first temperature sensor to manage thermal energy generation in the WCD.

22. The computer system of claim 21, further comprising: means for maintaining a currently implemented thermal management policy if the temperature measurement received from the first temperature sensor is less than the first temperature threshold.

23. The computer system of claim 21, further comprising: means for modifying a currently implemented thermal management policy if the temperature measurement received from the first temperature sensor is greater than the first temperature threshold.

24. The computer system of claim 21, wherein the health-tracking sensors comprise at least one of a heart-rate monitor, a pulse monitor, and an O2 sensor.

25. The computer system of claim 21, wherein the determined user proximity state defines that the WCD is proximal to a user and the first temperature threshold is associated with the touch temperature of the WCD.

26. The computer system of claim 21, wherein the determined user proximity state defines that the WCD is in a docked state and not physically proximal to a user.

27. The computer system of claim 21, wherein the determined user proximity state defines that the WCD is not physically proximal to a user and the first temperature threshold is associated with the operating temperature of a processing component in the WCD.

28. The computer system of claim 27, further comprising:
means for setting a second temperature threshold that is associated with a second temperature sensor in the WCD;
means for comparing the second temperature threshold with a temperature measurement received from the second temperature sensor; and
means for, based on the comparison of the first temperature threshold with the temperature measurement received from the first temperature sensor, modifying a currently implemented thermal management policy, wherein the modified thermal management policy prevents the second temperature sensor measurement from exceeding the second temperature sensor threshold.

29. The computer system of claim 21, further comprising means for also using one or more monitored signals from one or more of a bio-impedance sensor, a gyroscope, an accelerometer, a temperature sensor, a pressure sensor, a capacitive sensor, a resistive sensor and a light sensor of the WCD to determine the user proximity state for the WCD.

30. The computer system of claim 27, wherein the first temperature threshold is associated with a maximum operating temperature of the processing component.

31. A computer program product comprising a non-transitory computer-usable medium having a computer-readable program code embodied therein, said computer-readable program code adapted to be executed to implement a method for managing thermal energy generation in a wearable computing device, said method comprising:
monitoring one or more health-tracking signals from one or more health-tracking sensors of the WCD;
based on the monitored one or more health-tracking signals, both providing corresponding health-tracking information and determining a user proximity state for the WCD;
based on the user proximity state, setting a first temperature threshold for a thermal management policy; and
comparing the first temperature threshold with a temperature measurement received from a first temperature sensor to manage thermal energy generation in the WCD.

32. The computer program product of claim 31, further comprising:
maintaining a currently implemented thermal management policy if the temperature measurement received from the first temperature sensor is less than the first temperature threshold.

33. The computer program product of claim 31, further comprising:
modifying a currently implemented thermal management policy if the temperature measurement received from the first temperature sensor is greater than the first temperature threshold.

34. The computer program product of claim 31, wherein the health-tracking sensors comprise at least one of a heart-rate monitor, a pulse monitor, and an O2 sensor.

35. The computer program product of claim 31, wherein the determined user proximity state defines that the WCD is proximal to a user and the first temperature threshold is associated with the touch temperature of the WCD.

36. The computer program product of claim 31, wherein the determined user proximity state defines that the WCD is in a docked state and not physically proximal to a user.

37. The computer program product of claim 31, wherein the determined user proximity state defines that the WCD is not physically proximal to a user and the first temperature threshold is associated with the operating temperature of a processing component in the WCD.

38. The computer program product of claim 37, further comprising:
setting a second temperature threshold that is associated with a second temperature sensor in the WCD;
comparing the second temperature threshold with a temperature measurement received from the second temperature sensor; and
based on the comparison of the first temperature threshold with the temperature measurement received from the first temperature sensor, modifying a currently implemented thermal management policy, wherein the modified thermal management policy prevents the second temperature sensor measurement from exceeding the second temperature sensor threshold.

39. The computer program product of claim 31, the method further comprising also using one or more monitored signals from one or more of a bio-impedance sensor, a gyroscope, an accelerometer, a temperature sensor, a pressure sensor, a capacitive sensor, a resistive sensor and a light sensor of the WCD to determine the user proximity state for the WCD.

40. The computer program product of claim 37, wherein the first temperature threshold is associated with a maximum operating temperature of the processing component.

* * * * *